United States Patent [19]
Rekow et al.

[11] Patent Number: 5,273,429
[45] Date of Patent: Dec. 28, 1993

[54] METHOD AND APPARATUS FOR MODELING A DENTAL PROSTHESIS

[75] Inventors: Dianne Rekow, Baltimore, Md.; Bruce Nappi, Reading, Mass.; Yang Zhu, St. Paul, Minn.

[73] Assignee: Foster-Miller, Inc., Waltham, Mass.

[21] Appl. No.: 864,884

[22] Filed: Apr. 3, 1992

[51] Int. Cl.⁵ ............................ A61C 5/00; A61C 5/10
[52] U.S. Cl. .................................. 433/215; 433/223
[58] Field of Search ............... 433/26, 196, 197, 218, 433/223, 215, 214

[56] References Cited

U.S. PATENT DOCUMENTS

| | | | |
|---|---|---|---|
| 4,663,720 | 5/1987 | Duret et al. | 433/214 X |
| 4,742,464 | 5/1988 | Duret et al. | 433/214 X |
| 4,837,732 | 6/1989 | Brandestini et al. | 433/223 X |
| 4,937,928 | 7/1990 | van der Zel | 433/223 X |
| 5,027,281 | 6/1991 | Rekow et al. | 364/474.24 |

FOREIGN PATENT DOCUMENTS

WO91/03989  4/1991  PCT Int'l Appl.

*Primary Examiner*—Gene Mancene
*Assistant Examiner*—Nicholas D. Lucchesi
*Attorney, Agent, or Firm*—Wolf, Greenfield & Sacks

[57] ABSTRACT

A technique for modeling dental prostheses for a selected posterior tooth is provided. The technique involves selecting a standard tooth form for the tooth from a library of standard tooth forms with a corresponding digital mapping being stored for each form. The stored tooth form is then bilaterally scaled in both the buccal/lingual dimension and the mesial/distal dimension based on measured data for teeth of the patient other than the selected tooth. The stored tooth is also aligned in six dimensions with the proximal and occluding teeth, the six dimensions including angular dimensions to compensate for both the curve of Spee and the curve of Wilson. The depth position of the tooth is obtained by matching mating cusps and grooves and adjusting the tooth position to compensate for the offset and, for mandibular teeth, by adjusting or scaling the height of the buccal cusp to compensate for offsets. The angle of the lingual cusp for mandibular teeth may also be adjusted to take into account functional considerations.

34 Claims, 4 Drawing Sheets

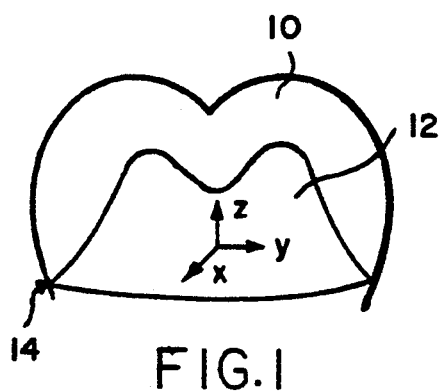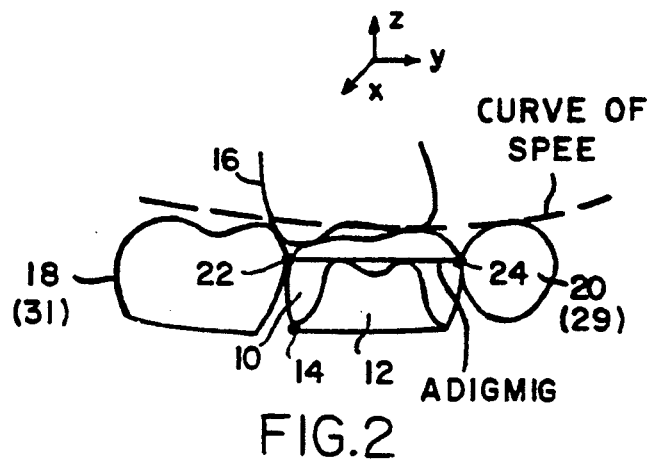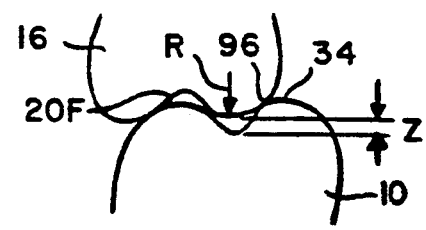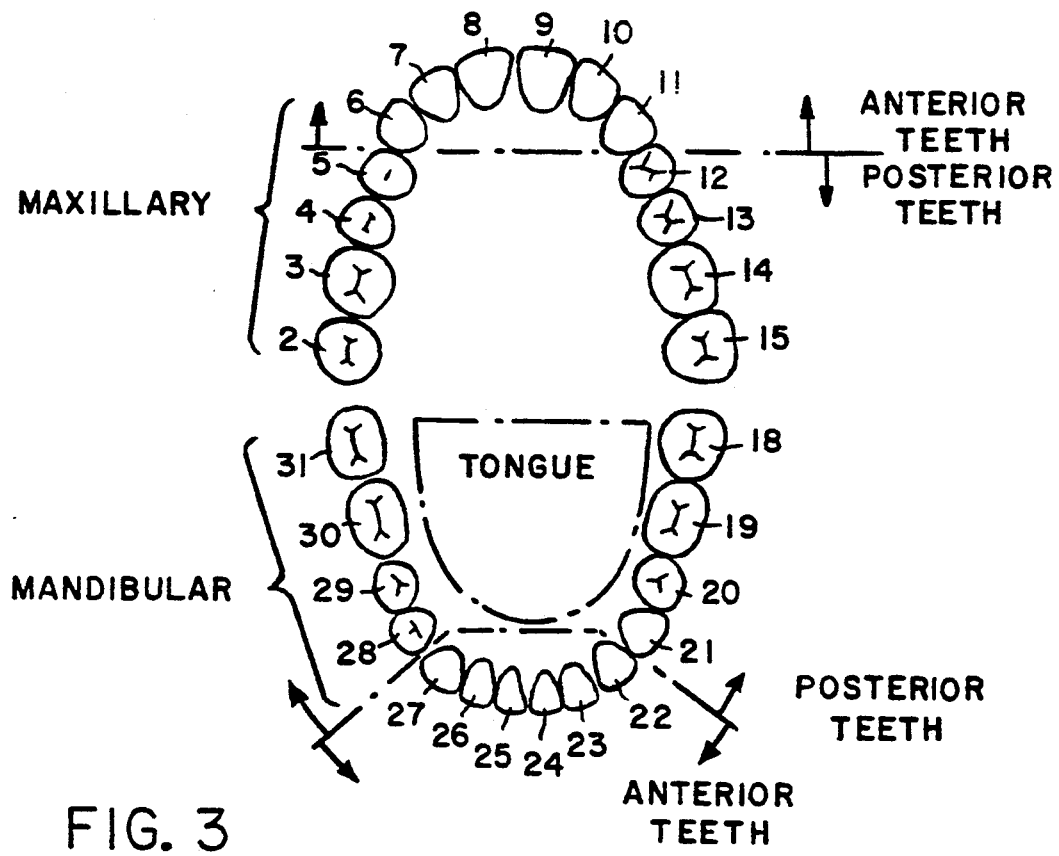

TOOTH-BASED:
    I = IDEAL TOOTH FORM
    P = PREPARED TOOTH
    O = OCCLUDING TOOTH
    A = ADJACENT/PROXIMAL TOOTH/TEETH
MORPHOLOGY-BASED
    SL = SLOPE
    SF = SURFACE
    C  = CUSP
    G  = GROOVE OR PIT
    R  = RADIUS
LOCATION ON TOOTH:
    M = MESIAL (TOWARD FRONT OF FACE)
    D = DISTAL (TOWARD BACK OF HEAD)
    B = BUCCAL (TOWARD CHEEK)
    L = LINGUAL (TOWARD TONGUE)
FIG. 6A
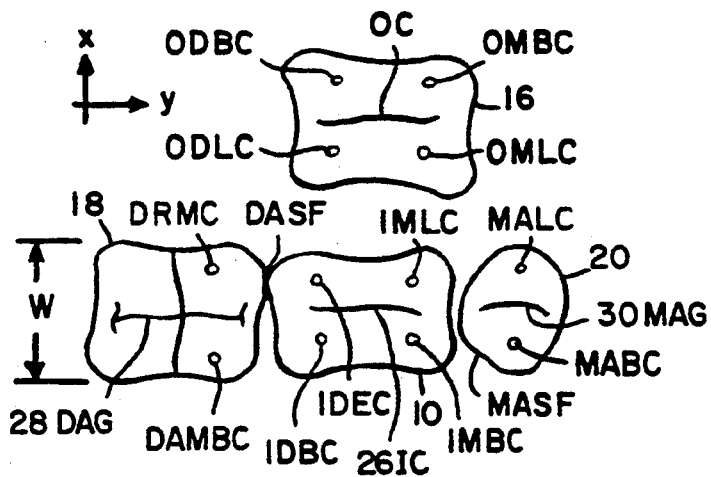
FIG. 6B
FIG. 7

METHOD AND APPARATUS FOR MODELING A DENTAL PROSTHESIS

FIELD OF THE INVENTION

This invention relates to a method and apparatus for modeling dental prostheses and more particularly to a method and apparatus for converting measurements taken on a patient's mouth into data suitable for operating a CAD/CAM machine to produce the prosthesis.

BACKGROUND OF THE INVENTION

Historically, dental restorations have been created through a lost wax casting technique. The dentist prepares a tooth, grinding it into the required shape to properly accept a restoration (such as a crown, inlay, or bridge). An impression of the prepared tooth and the teeth surrounding it is made. Another impression is made of the opposing teeth that will contact the restoration when it is seated in the patient's mouth. Dental stone is poured into the impressions, forming a set of models. The region of the prepared tooth is manipulated so that it can be removed and reinserted into position relative to the other teeth. A technician creates a wax pattern of the restoration to be cast.

The design of the chewing surface of the wax pattern, and ultimately the casting made from it, are critical for proper function and patient comfort. The chewing surface must properly contact the surface of the opposing tooth when the upper and lower teeth are together, but there must be no interference between the upper and lower surfaces when the jaw moves from side to side during functions like chewing. If interferences occur, teeth become very sensitive and, in some cases, a root canal treatment may be required; the jaw functions improperly, leading to temporalmandibular joint disorders; or one tooth may move, because of resultant forces during function, to a position that is physiologically unstable.

The surface shapes of any dental restoration are unique to the tooth being restored; the surface of the restoration is not simply a reflection of the surface of the occluding tooth. The surface must incorporate morphologic characteristics of the tooth to be restored which are, for the most part, uniform for a given tooth for all people regardless of sex, race, age and other factors. There are generally two to five such tooth forms for each tooth in the mouth. For example, a mandibular first molar has three buccal and two lingual cusps in a relatively fixed relationship to each other for all human first molars. The surface must also incorporate the unique characteristics that permit it to function properly in the patient's mouth. This requires that the positions of cusps and grooves or valleys on the tooth may have to be raised or lowered to provide the appropriate contacts without interference.

In the current state of the art, a pattern (usually wax or some check bite material) is made of the interdigitation between the upper and lower teeth in their static, closed position. Generally little information is gathered directly from the patient about the envelope of motion of lower teeth past the upper teeth during function. Instead, the pattern is inferred from the anatomy of adjacent and opposing teeth and the dentist makes necessary adjustments by grinding the surface of the restoration when it is inserted. This method is time consuming and has questionable accuracy.

In some cases, information about the motion of the jaw is obtained directly from the patient. Two techniques are generally used; (1) a face bow transfer and (2) a functionally generated path. To obtain a face bow transfer, the dentist uses a special device to locate the axis of rotation of the lower jaw relative to the upper jaw. Using this information, the casts are mounted on an articulator that preserves these relationships. The motion of the teeth through their entire range of motion is inferred from the articulator and casts and is used to design the wax pattern for the restoration. This technique is time consuming and may or may not improve the precision of the design of the chewing surface of the restoration.

The functionally generated path technique permits a clinician to obtain information defining a functionally balanced occlusion, unique to each patient, without the need for a dental articulator. This technique is, however, time-consuming, complicated and difficult to master.

The advent of CAD/CAM systems for dental restorations has made automation of the design of dental restorations possible. CAD/CAM dental restoration systems are, for example, described in U.S. Pat. No. 4,742,464 issued May 3, 1988 to Duret, et al, U.S. Pat. Nos. 4,766,704 and 4,837,732 issued Aug. 30, 1988 and Jun. 6, 1989, respectively, to Brandestini et al and U.S. Pat. No. 5,027,281 issued Jun. 25, 1991 to Rekow et al. The system described in the Brandestini patents does not account for the occlusal surface of the tooth with the automation. Instead, the dentist must shape the occlusal surface of the restoration at the time that it is placed in the patient's mouth. With the system described in the Duret, et al patent, the dentist must design the chewing surface of the tooth through a series of interactive manipulations.

By contrast, the system disclosed in the Rekow, et al patent utilizes a suitable probe to take measurements in the patient's mouth of the dental prep and of at least the surrounding teeth. This information is then utilized to modify a standard tooth form for the tooth being restored, dimensions for which are stored in a computer memory in a form suitable for operating a CAD/CAM machine. Finally, this patent teaches a CAD/CAM machine which may be utilized for converting the modified tooth form data into the desired dental restoration.

While the Rekow, et al system permits a restoration to be automatically generated, it is not capable of providing an exact match for the chewing or occlusal surface. This system also does not fully account for functional requirements during chewing and other mouth movements, such requirements including proper angling of the lingual cusp of posterior mandibular teeth. Thus, the dentist or other clinician is forced to compensate for inaccuracies and inconsistencies when the restoration is placed in the patient's mouth by using a drill or other tool to eliminate interferences in mating at the occlusal surfaces and any functional interferences. Depending on the degree of inaccuracy in the originally generated restoration, this process can be time consuming and is unpleasant for the patient.

Further, the stored tooth form must be scaled to the proper dimensions for the patient's mouth. In the Rekow patent, this is done by measuring the gap and performing height and width measurements on adjacent (proximal) teeth, and then using the ratio of these dimensions to the corresponding dimensions of the stored tooth form to produce a scaling factor to be applied to the dimensions of the scaled tooth form. Unfortunately, such gross scaling may not always provide satisfactory results and improved scaling techniques are, therefore, required.

Further, the tooth form needs to be angularly oriented relative to the adjacent teeth in at least three dimensions. While the prior art has oriented the tooth about the depth axis so that the groove in the restoration is aligned with the grooves of the one or more adjacent teeth, the prior art has not specifically addressed the curve of Spee which is the angle of the tooth from the front of the mouth toward the rear of the mouth for posterior teeth, nor has such art addressed the curve of Wilson, the angle of the teeth in a direction away from the cheek and toward the tongue. These angles must be taken into consideration in the modeling of the tooth form in order for a properly fitting tooth to be machined.

A need, therefore, exists for an improved technique for modeling dental restorations from measurements of a patient's mouth and related information to produce CAD/CAM coordinates for fabricating a restoration or other dental prosthesis. Such technique should provide consistent and accurate matching on the occlusal surface so that little, if any, work is required on the restoration after it is placed in the patient's mouth and, in particular, should take into account functional factors on the occlusal surface. Such a modeling technique should also provide more accurate scaling of a stored tooth form model to the dimensions of the patient's mouth and should take into account all of the angular degrees of freedom of the tooth and the unique demands of jaw motion in the modeling thereof.

SUMMARY OF THE INVENTION

In accordance with the above, this invention proides a technique for the modeling of dental prostheses or restorations for a selected posterior tooth of a patient. The technique involves selecting a standard tooth form for the tooth from a library of standard tooth forms with corresponding digital mapping data being stored for each such form. The stored tooth form is then scaled in the buccal/lingual dimension and in the mesial/distal dimension based on measured data for teeth of the patient other than the selected tooth. The stored tooth form is aligned in at least two dimensions with at least one proximal tooth and the occluding tooth for the selected tooth. The heights and depths for the cusp and depressions in the stored tooth form are also adjusted to match mating depressions and cusps, respectively, of the occluding tooth.

For a preferred embodiment, scaling in the buccal/lingual direction is accomplished by determining the ratio of the buccal/lingual spacing between selected cusps measured for a given tooth of the patient other than the selected tooth, the buccal/lingual spacing for the same cusps for the stored tooth form, and utilizing the determined ratio to scale the stored tooth form. Scaling in the mesial/distal dimension is performed by determining the ratio of the spacing between the contact points measured for the mesial and distal proximal teeth to the mesial/distal dimension of the stored tooth form and utilizing the determined mesial/distal ratio to scale the tooth form in the mesial/distal dimension.

For preferred embodiments, a reference point is established on the stored tooth form and the position of the reference point is maintained constant during at least one of the scaling steps, with scaling being performed on either side of the reference point. The reference point may be a pit in the stored tooth form which mates with the cusp on the occluding tooth or vice versa. This type of scaling is also referred to as bilateral scaling. For one embodiment, where the selected tooth has at least two cusps spaced in the mesial/distal dimension, bilateral scaling in this dimension is performed by maintaining the mesial/distal location of these cusps constant during the scaling operation.

During the aligning step, the angle in the buccal/lingual dimension and position of the groove for at least one of the proximal teeth for the selected tooth are determined, and the angle and buccal/lingual dimension position of the groove for the stored tooth form are aligned with the determined angle and position for the proximal tooth or teeth. The aligning step may also include the step of aligning the stored tooth form in the mesial/distal dimension so that there is alignment of at least one mating cusp and pit of the tooth form and the occluding tooth.

The aligning step may also include the steps of determining the angle from the buccal cusp tip to the lingual cusp tip for at least one related tooth, for example a proximal or contra lateral tooth, and tipping the angle of the stored tooth form so that its buccal cusp tip/lingual cusp tip angle matches that of the at least one proximal tooth. Another alignment is performed by determining the angle in the mesial/distal direction for teeth in the area of the selected tooth and tipping the stored tooth form in the mesial/distal direction to the determined angle. This step may be performed by determining the angle for a line connecting the grooves for the mesial and distal proximal teeth and tipping the stored tooth form so that the angle of a line extending from the mesial to the distal end of the groove for the stored tooth form is the same as the determined angle.

The adjusting step may further include the step of determining the curve for a cusp of the proximal tooth which fits in the groove of the selected tooth, fitting the curved cusp in the mating groove of the stored tooth form, determining the offset between the tip of the cusp when positioned in the groove and the deepest point of the groove and changing the groove location for the stored tooth form to compensate for such offset. The groove location change may be effected by adjusting the stored tooth form in the depth dimension to compensate for the offset. The adjusting step may also include the steps of determining the difference between the height of a cusp of the stored tooth form and the depth of a mating groove in the occluding tooth, and changing the height of the cusp to compensate for such difference. The height change may be effected by locally scaling the stored tooth form in the depth dimension to compensate for such difference.

The technique may also include determining the slope for the lingual cusp of mandibular teeth by use of functionally generated occlusion information. In particular, a functional model of the occluding tooth is produced and a plurality of points on the generated surface for at least one of the lingual cusps may be selected on the functional model. Such points are used to determine a slope for the generated surface and the determined slope is utilized to set the slope for at least one lingual cusp. The slope so determined is preferably dropped by an angle of N° from the determined slope to allow sliding clearance. N° is preferably less than 30° and, for a preferred embodiment, is approximately 10°.

The foregoing and other objects, features and advantages of the invention will be apparent from the following more detailed description of the preferred embodiments of the invention as illustrated in the accompanying drawings.

IN THE DRAWINGS

FIG. 1 is a front sectional diagrammatic view illustrating a crown positioned on a preparation.

FIG. 2 is a front diagrammatic view illustrating the prep, which is assumed to be a posterior mandibular tooth, positioned with the two proximal teeth and an occluding tooth.

FIG. 3 is a top diagrammatic view illustrating the teeth normally present in a person's mouth (with the exception of the wisdom teeth) and a numbering system frequently used for such teeth.

FIG. 4 is a side diagrammatic view of a posterior mandibular tooth.

FIG. 5 is an enlarged side diagrammatic view of a posterior mandibular tooth and of the mating or occluding posterior maxillary tooth.

FIG. 6A is a chart of nomenclature used for various ones of the figures.

FIG. 6B is an occlusal surface diagrammatic view of tooth No. 30, of the proximal and teeth for tooth 30 of the occluding tooth (shown inverted) for tooth No. 30 which contains the nomenclature used to identify various features on these teeth called out in the flow diagram of FIG. 9.

FIG. 7 is a sectional view of a functionally generated path for a typical tooth.

DETAILED DESCRIPTION

Figure 8:
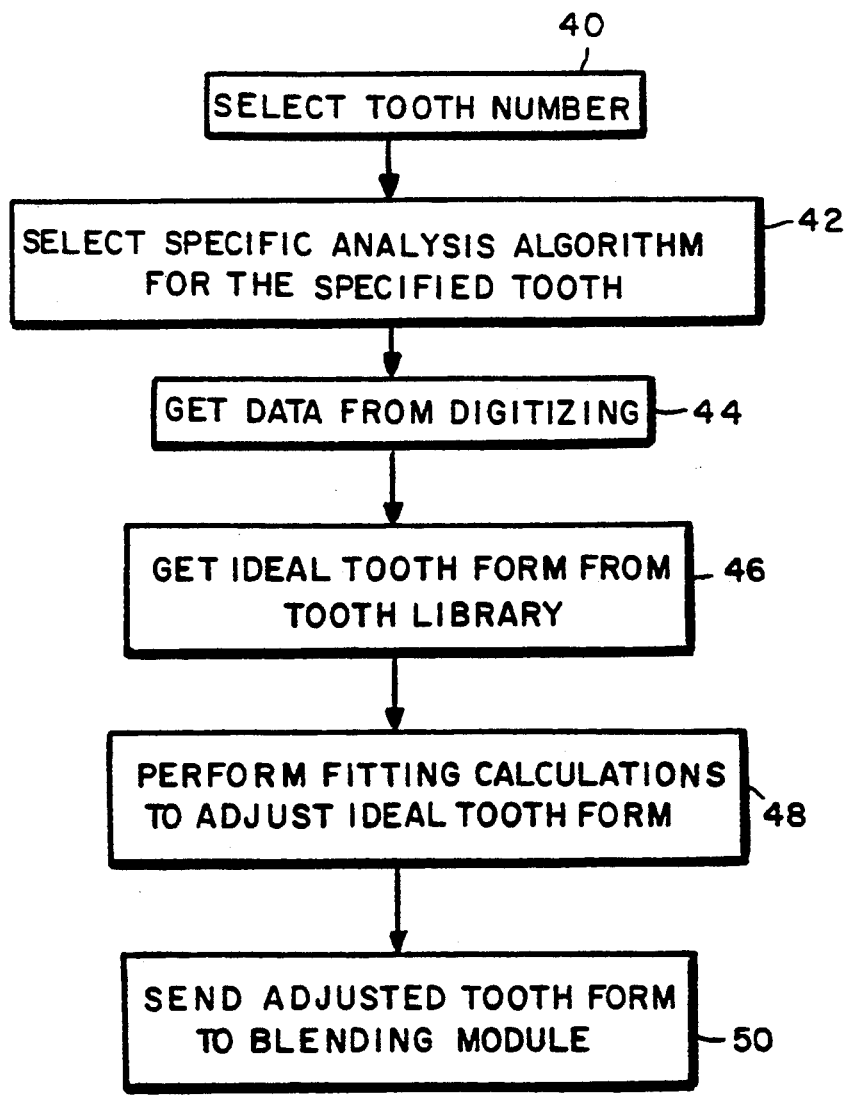
FIG. 8 is a generalized flow diagram for a crown modeling in accordance with the teachings of this invention.

While the teachings of this invention are applicable to a variety of dental restorations, including bridges, inlays and outlays, they find primary application in the modeling of crowns for a person's posterior teeth. The following discussion will, therefore, be with respect to such an application. However, it is not the intent that the invention be limited to this particular application.

FIGS. 1 and 2 illustrate the manner in which a crown 10 is mounted in a patient's mouth. As a first step, the dentist forms what is left of the patient's tooth into a prepared tooth (prep) 12 from which roots extend into the upper or lower jaw of the patient. However, the invention is not limited to the mounting of a crown to a prep. The invention may also be utilized for crowns being mounted to dental implants or to any other suitable base in the patient's mouth.

There are at least four criteria for the acceptance of a crown restoration. The first of these criteria is marginal fit. This relates generally to the fit between the crown 10 and prep 12, and in particular to the fit of the crown at the interface between the restoration and the prep. The mechanism for effecting proper marginal fit is discussed in copending application Ser. No. 07/862,980, filed Apr. 3, 1992 and the meeting of this criteria does not form part of the present invention.

The second criteria for acceptance involves occlusal fit. When the patient closes his mouth, there should not be any excess pressure between the occlusal tooth 16 (FIG. 2) and the crown or restoration 10 at any point on the mating or occlusal surfaces. As previously indicated, such pressure can traumatize dental nerves leading to tooth sensitivity and pain, and can also lead to improper jaw function leading to jaw disorders. Other problems may also result. One of the primary concerns of this invention is to assure that a restoration which is constructed using the CAD/CAM parameters generated by the modeling techniques of this invention will provide a sufficiently accurate fit between the occluding surfaces of the restoration 10 and tooth 16 so that little, if any, drilling or other procedures are required to eliminate interferences once the restoration is placed in the patient's mouth.

The third criteria for acceptance is interproximal fit. A piece of dental floss should "snap" as it passes between the restoration and an adjacent or proximal tooth. The modeling techniques of this invention are also designed to assure proper interproximal fit.

The final criteria for accepting a restoration is functional fit. As the teeth move through their normal excursions, there should not be interference between the restoration and occlusal surface of tooth 16. This invention also assures that the model restoration has a proper functional fit, again avoiding the need for drilling and other corrective procedures once the restoration has been placed in the patient's mouth.

In general terms, in order for the restoration to fit properly, it must be of proper size for the mouth of the patient. In particular, it must fit in the space in the patient's mouth between contact points 22 and 24 of the distal and mesial proximal teeth 18 and 20, respectively, must match the width W (FIG. 6B) of at least one of the proximal teeth and be of proper height H (FIG. 4). The tooth must also be properly aligned in the mouth with multiple degrees of freedom. This includes aligning the central groove 26 (FIG. 6) of the restoration 10 with the central grooves 28 and 30 for at least one of the proximal teeth both in the X direction and angularly. When the tooth has been properly scaled and is oriented in this way, the position in the Y direction (i.e. the mesial/distal direction) for the tooth is established.

For a manidublar posterior tooth, the central groove 26 must also mate with the lingual cusp 32 of the occluding tooth 16 (FIG. 5). Conversely, for a maxillary tooth, the lingual cusp 32 must mate with the groove 26 of the occluding mandibular tooth. This generally establishes the position for the tooth in the X or buccal/lingual direction.

The height H of the cusp is determined by mating grooves by functional considerations and for the buccal cusp of a maxillary tooth, by esthetics.

In addition to the angular orientation of the tooth about the Z axis to align groove 26 with the grooves of the proximal teeth, angular orientations about the X and Y axis are also important. FIG. 2 shows what is sometimes referred to as the curve of Spee wherein the teeth angle downward slightly when extending in the forward to the rear (mesial-to-distal) direction. For an ideal fit, the restoration must be angled slightly about the Y axis so as to align with the curve of Spee.

FIG. 4 shows that mandibular posterior teeth are also angled slightly in the lingual direction (away from the cheek and toward the tongue). This is referred to as the curve of Wilson. Again, in order to achieve an ideal fit, the restoration must be angled about the Y axis to match this inward slope for the adjacent teeth.

Finally, functional considerations must be taken into account in the modeling of the restoration and in particular the slope for the lingual cusp 34 of mandibular posterior teeth must be angled so as not to create interference during chewing or other mouth functions. The following discussion will indicate how the various operations indicated above are performed when modeling in accordance with the teachings of this invention.

The general operation of a system utilized to practice this invention is illustrated in FIG. 8. The first step, step 40, in this operation is to select the tooth which is to be restored. Referring to FIG. 3, it is seen that each tooth in the patient's mouth is assigned a number from 1 to 32. Maxillary teeth 1 and 16 and mandibular teeth 17 and 32, which are third molars or wisdom teeth, are not shown in this drawing, but would be positioned next to teeth 2, 15, 18 and 31, if present. The reason these teeth are not shown in FIG. 3 is that, when problems develop in these teeth, they are generally extracted rather than having restorations performed thereon. The posterior teeth in FIG. 3 are the teeth numbered 2-5, 12-15, 18-21 and 28-31. During step 40, the number for the tooth to be restored is selected.

During step 42, the next step in the operation, the specific analysis algorithm for the tooth selected during step 40 is retrieved. While the concepts of this invention are basically the same for all of the posterior teeth, differences in the number and placement of cusps and grooves in various ones of such teeth result in slight differences in the specific steps performed for modeling a given tooth. There are also some differences in the steps required for mandibular and maxillary teeth. Therefore, a separate algorithm is required for each tooth; however, there are substantial elements of similarity among all of the algorithms.

From step 42, the operation proceeds to step 44 to get the data which was taken from measurements on the patient's mouth and digitized. The before mentioned copending application, Ser. No. 07/862,980 describes the technique for obtaining and digitizing data for prep 12 and for other teeth in the mouth including, in particular, proximal teeth 18 and 20 and occluding tooth 16. At least relevant portions of these digitized measurements are retrieved during step 44.

During step 46, an idealized tooth form is retrieved from a stored library of tooth forms. As discussed above, there is substantial uniformity in the shape of a given tooth for all persons regardless of age, sex, race, and other factors. Thus, the number and size of the cusps and grooves for a given tooth number and the relative positions on the tooth of these cusps and grooves are fairly consistent for a given tooth. A limited number of from one to five tooth forms may therefore be stored, depending on the diversity of patients, for each tooth, and the operator may select the appropriate one of the tooth forms for the given patient and tooth based on information known for the patient and on a gross observation of the patient's mouth and teeth. What is retrieved during step 46 is a set of parameters for the tooth form, which parameters are in X, Y, Z coordinates that collectively define the outer contour of an ideal tooth.

During step 48, the next step in the operation, various operations are performed utilizing the data obtained during step 44 and the parameters of the standard tooth form to modify the standard tooth form so as to be properly scaled, aligned in at least six dimensions, sized and angled to fit properly in the patient's mouth. The operations performed during step 48 vary slightly from tooth to tooth. Later in this section, the operations performed during step 48 for mandibular molar 30 are described in detail and variations required on these operations for other posterior teeth are discussed.

Once step 48 has been completed, the surface shape parameters for the adjusted tooth form may be transferred to additional algorithms that link the adjusted tooth surface data with margins and preparation surface data obrtained, for example, from the output for the beforementioned copending application. The combined data are then processed by yet another algorithm that generates data for use by a suitable CAD/CAM machine to fabricate restoration 10. The aforementioned Rekow patent teaches one system which might be utilized for producing a dental restoration from a set of X, Y, Z parameters for a modified tooth form.

Figure 9:
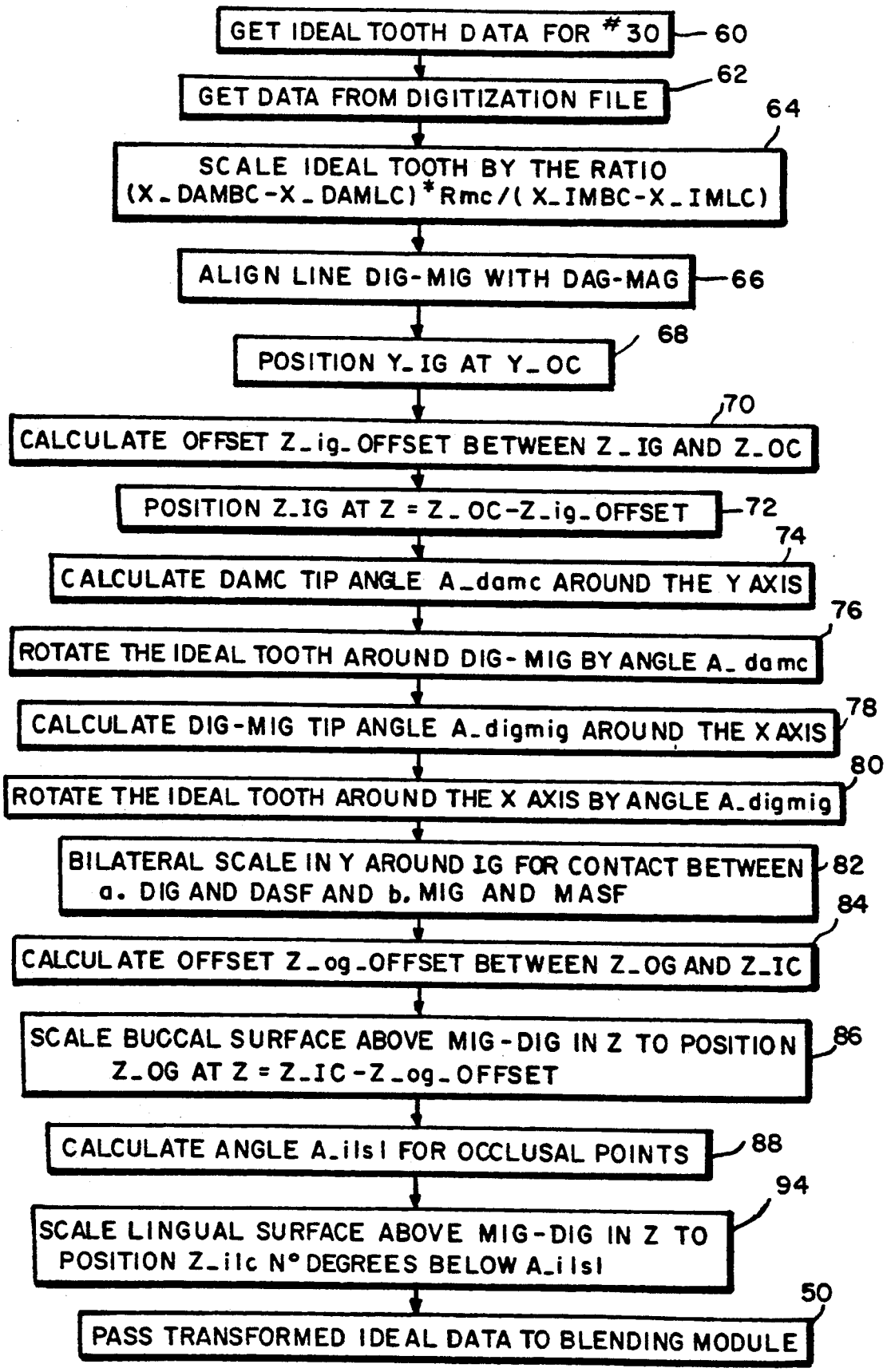
FIG. 9 is a detailed flow diagram of a portion of the crown modeling operation in accordance with the teachings of this invention for a No. 30 molar.

In conjunction with the discussion of the flow diagram chart in FIG. 9 for the modeling of the No. 30 molar, reference should be had to FIGS. 6A and 6B for an explanation of the nomenclature used in conjunction with this flow diagram. FIG. 6A contains a chart indicating the significance of the abbreviations utilized. Thus, IMBC would be the mesial buccal cusp for the ideal tooth form. DAG is the groove for the distal adjacent tooth. In FIG. 6B, the appropriate nomenclature is applied to each element shown in the drawing.

Referring now to FIG. 9, the first step in this operation, step 60 is the same as step 46, namely to retrieve from the stored library the appropriate ideal tooth form for tooth 30. Similarly, during step 62, the appropriate data for tooth 30 is retrieved from the digitized measurements. This is the same as step 44, but is specific for tooth 30.

The next step in the operation, step 64, is to scale the ideal tooth form in the buccal/lingual or X direction. In accordance with the teachings of this invention, this scaling is done based on the buccal/lingual spacing of the tooth cusps rather than on the tooth walls since, for a proper fit, it is the cusps that must match. Thus, during step 64, two operations are performed. First, the spacing in the Y direction between the cusps DAMBC and DAMLC is determined. Then, this value is multiplied by a constant spacing ratio which is a function of the tooth for which the restoration is being performed, tooth 30 in this case, and the tooth on which the cusp measurements were performed (distal tooth 31 in this instance). As seen from the following chart, this constant for tooth 30 where the cusp measurements are taken on tooth 31 is 1.121.

TABLE 1

| Restored Tooth #/Measured Tooth # | Spacing Ratio |
| --- | --- |
| 31/32 | 1.000 |
| 30/31 | 1.127 |
| 29/30 | .839 |
| 28/29 | .924 |
| 2/1 | 1.183 |
| 3/2 | .986 |
| 4/3 | .960 |
| 5/4 | .966 |

The scale factor is then determined by dividing the product of the cusp spacing for the distal tooth times the constant by the cusp spacing for the ideal tooth form. The ideal tooth form is then multiplied by this scale factor to adjust its size in the buccal/lingual or X dimension.

Each ideal tooth form has a reference point on the occlusal surface or at other locations, with the position of this reference point being maintained constant during scaling operations for the preferred embodiment. Thus, scaling occurs on either side of the reference point rather than with reference to the buccal or lingual side of the tooth. Scaling in this manner is sometimes referred to herein as bilateral scaling.

The next step in the operation, step 66, is to align IG line 26 with a line connecting groove DAG with groove MAG. This involves both rotating the coordinates of the ideal tooth form around the Z or depth axis so that the groove 26 is properly oriented and moving the groove laterally in the X direction so that groove 26 aligns with the line connecting the grooves of the two proximal teeth. From step 66, the operation proceeds to step 68 to position the cusp OC of the occluding tooth 16 in the groove IG of the ideal tooth. Referring to FIG. 5, this means that the cusp 32 is positioned in the groove of the restoration model 10. This perfects the X orientation for the model.

Referring still to FIG. 5, the offset Z between the end of the cusp 32 and the deepest point in the groove G is determined during step 70. This step involves the preliminary step of approximating the curvature of the occluding cusp from measurements previously taken. This curve is fitted in the groove of the stored tooth form as far as it will go, as shown in FIG. 5, and the resulting offset Z is determined. During step 72, the position of the ideal tooth form is adjusted in the Z dimension to position the groove of the stored tooth to the position of the occluding cusp minus the offset. This operation is accomplished by moving the entire ideal tooth form in the Z direction.

During step 74, the next step in the operation, the angle between the tips DAMBC and DAMLC (FIG. 6B) is determined. From FIG. 4, it can be seen that this angle is the angle $A_{damc}$ referred to in step 74. Once the angle $A_{damc}$ is determined during step 74, the ideal tooth form is rotated about the Y axis through this angle during step 76 so that $A_{damc}$ for the ideal tooth form is the same as for distal tooth 18.

From step 76, the operation proceeds to step 78 during which the angle Adigmig between the line connecting the points 22 and 24 and the horizontal is determined. This angle is shown in FIG. 2. During step 80, the ideal tooth form is rotated around the X axis by this determined angle in order to properly align the tooth form with the adjacent teeth in this dimension.

The next step in the operation, step 82, is to bilaterally scale the idealized stored tooth form in the Y (i.e. mesial/distal) dimension around the central reference point to achieve the desired interproximal fit for the idealized model with the distal tooth 18 and the mesial tooth 20 (teeth 31 and 29 in FIG. 3). Typically, there is a single point of contact with each of the proximal teeth, which point is slightly buccal to the grooves. However, the exact contact point may be different for some patients. Bilateral scaling may be with respect to the previously mentioned reference point of the stored tooth form with the ideal tooth form being expanded or contracted on either side of the reference point to have the desired interproximal fit with the appropriate adjacent tooth. Alternatively, in some applications it may be desirable to keep the spacing in the Y dimension between IMBC and IDBC and between IMLC and IDLC constant with scaling being performed only on the portion of the ideal tooth form external to the cusps. In other words, the cusp positions are maintained constant.

Referring again to FIG. 5, the offset ZOF between the buccal cusp of the stored tooth form and the groove of the occluding tooth 16 is determined step 84). During step 86, the height of the buccal cusp of the stored tooth form is adjusted to compensate for the offset. This may be accomplished by raising or lowering the cusp, but is preferably accomplished by locally scaling the buccal cusps.

During step 88, the angle for two or more points, on the lingual side of a functionally generated path 92 (FIG. 7) is determined. This is basically the angle through which the lingual or working cusp of the occluding tooth 16 moves in the buccal/lingual direction during chewing or other functions. During step 94, the angle of the groove surface 96 of the lingual cusp for the stored tooth form is adjusted to the angle determined during step 88 and may be dropped an additional number of degrees so as to assure that there is no contact or interference with this cusp during function. While the drop angle N may be up to 30°, it is approximately 10° for the preferred embodiment. This operation is an important feature of the invention. When step 94 has been completed, the operation proceeds to step 50 (also see FIG. 8) to pass the digitized coordinates for the adjusted tooth form to the algorithm that adds the remaining surfaces.

While for the example of tooth 30 discussed above, there is both a mesial and distal proximal tooth for the tooth having the restoration, the invention can also be practiced where this is not the case. For example, assume that the restoration is for tooth 31 rather than for tooth 30 and that wisdom tooth 32 is missing. In this situation, step 76 would be performed using the mesial tooth, tooth 30, rather than the distal tooth. For step 66, the DAG/MAG line would be replaced by a line from the OC point of the occluding tooth data to MAG. Steps 68, 70 and 72 would be performed as described above and, for step 74, the tip angle would be calculated for the mesial tooth rather than the distal tooth. For step 82, bilateral scaling would be performed to obtain proper contact at the mesial tooth surface and the same scale factor would be applied on the distal sides of the tooth. The remaining steps are performed the same as described earlier for the No. 30 molar.

There are also slight differences when modeling a restoration for a tooth such as tooth 28 or 29 having a different number of cusps than tooth 30. In particular, for tooth 28, there is a problem in that the mesial tooth, tooth 27, does not have a groove, but has only a cusp. Therefore, for step 66, it is necessary to compute the position and angle of the line DAC/MAC which is a line connecting the cusp of the two teeth proximal to tooth 28. DAG/MAG is then assumed to be a line parallel to the line DAC/MAC which passes through DAG, DAG being the groove of tooth 29. Alignment during step 66 is then performed on this DAG/MAG line. Further, this tooth does not have a tip angle since it has only a single cusp. Therefore, steps 74 and 76 are not performed for this tooth. The absence of a lingual cusp also means that steps 88 and 94 need not be performed.

While in the discussion above, only teeth on the right side of the mouth have been discussed, the operations performed for each tooth on the left side of the mouth, teeth 12–15 and 18–21, would be mirror images of those described for the corresponding tooth on the right side of the mouth. Also, for maxillary teeth, it is required that the buccal tips align with adjacent teeth for esthetic reasons and that both sets of cusps avoid interference during function.

Further, in order to enhance fit, certain additional steps could be performed. For example, after bilateral scaling step 82, the stored profiles for the proximal surfaces of the distal and mesial teeth could be compared against the stored profiles for the adjacent surfaces of the modified stored ideal tooth form and any interferences found as a result of such comparison could be eliminated. Similarly, after step 94 has been completed, the stored records for the occlusal surface of mating tooth 16 could be compared against the occlusal surface of the modified ideal tooth form and any interferences found as a result of such comparison could also be eliminated. In addition, while steps 70, 72, 84,86, 88 and 94 have made adjustments for adjacent buccal or lingual cusp based on measurements and analysis for one cusp of the pair, the calucations and adjustment steps in each instance could be performed separately for each cusp to obtain an enhanced fit.

Further, while the teachings of this invention are primarily applicable to the production of dental prostheses such as crowns or other restorations, these techniques could also be utilized in the fabrication of splints or other devices to direct the motion of a patient's jaw during function. Such devices are used in the treatment of temporal mandibular joint disorders. Utilizing the teachings of this invention, the movement of the jaw can be completely and accurately determined and integrated into the surfaces of the splints.

The techniques of this invention could also be utilized in teaching the design of the occlusal surface for dental restorations and in particular the required modifications to integrate the unique characteristics of each patient. They could also be used to mathematically test various theories as to the ideal occlusal surface for restorations.

Finally, while in the discussion above, it has been assumed that the teachings of this invention are being practiced by use of a programmed general purpose computer having a memory in which the tooth form library and the measured data from the patient's mouth are originally stored, and from which they are transferred to a working memory for performance of the modeling, this is not a limitation on the invention. In particular, a special purpose computer could be designed for performing the functions of this invention, or these functions could be performed with some combination of hardware and software.

Thus, while the invention has been particularly shown and described above with reference to preferred embodiments, the foregoing and other changes in form and detail may be made therein by one skilled in the art without departing from the spirit and scope of the invention.

What is claimed is:

1. A method for modeling a dental prosthesis for a selected posterior tooth of a patient comprising the steps of:
    a) selecting a stored standard tooth form for the selected tooth from a library of standard tooth forms, a corresponding digital mapping being stored for each of said tooth forms;
    b) determining the ratio of the buccal/lingual spacing between selected cusps for the standard tooth form stored for the selected tooth to the buccal/lingual spacing for said selected cusps measured for a given tooth of the patient other than said selected tooth;
    c) utilizing said ratio to scale the stored standard tooth form in the buccal/lingual dimension;
    d) determining the mesial/distal ratio of a measured spacing between contact points for the mesial and distal proximal teeth with the selected tooth to the mesial/distal dimension of the stored standard tooth form;
    e) utilizing the determined mesial/distal ratio to scale the selected standard tooth form in the mesial/distal dimension;
    f) aligning the selected standard tooth form in at least two dimensions with at least one proximal tooth and the occluding tooth for said selected tooth; and
    g) adjusting selected portions of the stored standard tooth form to match mating portions of said occluding tooth.

2. A method as claimed in claim 1 wherein the given tooth for step (b) is a proximal tooth for the selected tooth.

3. A method as claimed in claim 2 wherein the given tooth for step (b) is the corresponding tooth on the opposite side of the mouth from said selected tooth.

4. A method as claimed in claim 1 wherein at least one of the cusp spacings of step (b) is multiplied by a stored value determined by the selected and given teeth to obtain a scale factor for step (c).

5. A method as claimed in claim 1 including the steps of establishing a reference point for said stored standard tooth form, and maintaining the position of said reference point constant during at least one of said at least one scaling step steps, the scaling being performed separately on either side of said reference point.

6. A method as claimed in claim 5 wherein said maintaining step is performed for both scaling steps.

7. A method as claimed in claim 5 wherein said reference point is a pit on the stored standard tooth form which mates with a cusp on said occluding tooth.

8. A method as claimed in claim 5 wherein said reference point is a cusp on the stored standard tooth form which mates with a pit on said occluding tooth.

9. A method as claimed in claim 1 wherein said aligning step (f) includes the steps of determining the angle and the buccal/lingual dimension position of the groove for at least one of said proximal teeth, and aligning the angle and the buccal/lingual dimension positions of the groove for the stored standard tooth form with the determined angle and position for the at least one proximal tooth.

10. A method as claimed in claim 1 wherein said aligning step (f) includes the step of aligning the stored standard tooth form in the mesial/distal dimension so that there is alignment of at least one mating cusp an pit of the tooth form and the occluding tooth.

11. A method as claimed in claim 1 wherein said aligning step includes the steps of determining the angle from the buccal cusp tip to the lingual cusp tip for at least one of said proximal teeth, and tipping the angle of the stored standard tooth form so that its buccal cusp tip lingual cusp tip angle matches that of the at least one proximal tooth.

12. A method as claimed in claim 1 wherein said aligning step includes the steps of determining the angle in the mesial/distal direction for teeth in the area of said selected tooth, and tipping the stored tooth form in the mesial-distal direction to the determined angle.

13. A method as claimed in claim 12 wherein said angle determining step includes the step of determining the angle for a line connecting the grooves for the mesial and distal proximal teeth, and wherein the tipping step includes the step of tipping the stored standard tooth form so that the angle of a line extending from the mesial to the distal end of the groove for the stored standard tooth form is the same as the determined angle.

14. A method as claimed in claim 1 wherein said adjusting step includes the steps of determining the curve for a cusp of the proximal tooth which fits in a groove of the selected tooth, fitting the curved cusp in a mating groove of the stored standard tooth form, determining the offset between the tip of the cusp when positioned in the mating groove and the deepest point of the mating groove, and changing the depth position for the store standard tooth form to compensate for such offset.

15. A method as claimed in claim 1 wherein said adjusting step includes the steps of determining the difference between the height of a cusp of the stored standard tooth form and the depth of a mating groove in the occluding tooth, and changing the height of the cusp to compensate for such difference.

16. A method as claimed in claim 15 wherein said height changing step includes the step of locally scaling the cusp portion of the stored standard tooth form to compensate for said difference.

17. A method as claimed in claim 1 including the step of determining the slope for the lingual cusps of mandibular teeth by use of functionally generated occlusal information.

18. A method as claimed in claim 17 wherein a functional model of the occluding tooth is produced; and wherein said slope determining step includes the steps of selecting two or more points on the lingual groove surface for at least one of the lingual cusps of said functional model, using said points to determine a slope for the groove surface, and utilizing the determined slope to set the slope for the at least one lingual cusp.

19. A method as claimed in claim 18 wherein said uitilizing step includes dropping the slope for the at least one lingual cusp by N° from the determined slope.

20. A method as claimed in claim 19 wherein N° is approximately 10°.

21. A method of modeling a dental prosthesis for a selected posterior tooth of a patient comprising the steps of:
selecting a stored standard tooth form for the selected tooth from a library of standard tooth forms, a corresponding digital mapping being stored for each of said tooth forms, each of said stored tooth forms having a predetermined reference point;
scalling the stored standard for tooth form for the selected tooth in the buyccal/lingual dimension and the mesial/distal dimension based on measured for teeth of the patient other than the selected tooth, scaling in at least one of said dimensions being a bilateral scaling wherein the position of the reference point of the bilateral scaling remains constant, a scaling being performed on either side of the reference point;
aligning the scaled standard tooth form in at least two dimensions with at least one proximal and the occluding tooth for said selected tooth; and
adjusting selected portions of the scaled standard tooth form to match mating portions of said occluding tooth.

22. A method as claimed in claim 21 wherein the selected tooth has at least two cusps spaced in the mesial/distal dimension; wherein said bilateral scaling step is in the mesial/distal dimension, and wherein, during such scaling, the mesial/distal spacing between said at least two cusps is maintained substantially constant.

23. A method of modeling a dental prosthesis for a selected posterior tooth of a patient comprising the steps of:
selecting a stored standard tooth form for the selected tooth from a library of standard tooth forms, a corresponding digital mapping being stored for each of said tooth forms:
scaling the stored standard tooth form for the selected tooth in the buccal/lingual dimension and in the mesial/distal dimension based on measured data for selected teeth other than the selected tooth;
aligning the stored standard tooth form in at least two dimensions with at least one proximal tooth and the occluding tooth for said selected tooth, said aligning step including the step of changing the angle for the standard tooth form about the depth axis and about at least one other axis; and
adjusting the selected portions of the stored standard tooth form to match mating portions of said occluding tooth.

24. A method as claimed in claim 23 wherein said changing step includes the steps of determining the angle from the buccal cusp tip to the lingual cusp tip for at least one related tooth, and tipping the angle of the of the stored standard tooth form so that its buccal cusp tip/lingual cusp tip angle matches that of the related tooth.

25. A method as claimed in claim 24 wherein said related tooth is a proximal tooth.

26. A method as claimed in claim 23 wherein said changing step includes the steps of determining the angle in the mesial/distal dimension for teeth in the area of said selected tooth, and tipping the stored standard tooth form in the mesial/distal dimension to the determined angle.

27. A method as claimed in claim 26 wherein said angle determining step includes the step of determining the angle for a line connecting the grooves for the mesial and distal proximal teeth of the selected tooth, and wherein the tipping step includes the step of tipping the stored standard tooth form so that the angle of a line extending from the mesial to the distal end of the groove for the stored standard tooth form is the same as the determined angle.

28. A method of modeling a dental prosthesis for a selected posterior tooth of a patient comprising the steps of:
selecting a stored standard tooth form for the selected tooth from a library of standard tooth forms, a corresponding digital mapping being stored for each of said tooth forms;
scaling the stored standard tooth form for the selected tooth in the buccal/lingual dimension and in the mesial/distal dimension based on measured data for selected tooth other than the selected tooth;

aligning the stored standard tooth form in at least two dimensions with at least one proximal tooth and the occluding tooth for said selected tooth; and adjusting the heights for selected portions of the stored standard tooth form to match mating portions of said occluding tooth, said adjusting step including the steps of determining the curve for a cusp of the proximal tooth which fits in a groove of the selected tooth, fitting the curved cusp in a mating groove of the stored standard tooth form, determining the offset between the tip of the cusp then positioned in the mating groove and the deepest point of the mating groove, and changing the depth dimension for the stored standard tooth form to compensate for such offset.

29. A method of modeling a dental prosthesis for a selected posterior tooth of a patient comprising the steps of:

selecting a stored standard tooth form for the selected tooth from a library of standard tooth forms, a corresponding digital mapping being stored for each of said tooth forms;

scaling the stored standard tooth form for the selected tooth in the buccal/lingual dimension and in the mesial/distal dimension based on measured data for selected teeth other than the selected tooth;

aligning the stored standard tooth form in at least two dimensions with at least one proximal tooth and the occluding tooth for said selected tooth; and adjusting the heights for selected portions of the stored standard tooth form to match mating portions of said occluding tooth, said adjusting step including the steps of determining the difference between the height of a cusp of the stored standard tooth form and the depth of a mating groove in the occluding tooth, and changing the height of the cusp to compensate for such difference.

30. A method as claimed in claim 29 wherein said height changing step includes the step of locally scaling the cusp of the stored standard tooth form in the depth dimension to compensate for said difference.

31. A method of modeling a dental prosthesis for a selected posterior tooth of a patient comprising the steps of:

selecting a stored standard tooth form for the selected tooth from a library of standard tooth forms, a corresponding digital mapping being stored for each of said tooth forms;

scaling the stored tooth form in the buccal/lingual dimension and in the mesial/distal dimension based on measured data for selected teeth other than the selected tooth;

aligning the stored standard tooth in at least two dimensions with at least one proximal tooth and the occluding tooth for said selected tooth;

adjusting the heights for selected portions of the stored standard tooth form to match mating portions of said occluding tooth; and determining the slope for the lingual cusps of mandibular teeth by use of functionally generated occlusal information.

32. A method as claimed in claim 31 wherein a functional model of the occluding tooth is produced; and wherein said slope determining step includes the steps of selecting a plurality of points on a lingual groove surface for at least one of the lingual cusps of said functional model, using said points to determine a slope for the groove surface, and utilizing the determined slope to set the slope for the at least one lingual cusp.

33. A method as claimed in claim 32 wherein said utilizing step includes dropping the slope for the at least one lingual cusp by N° from the determined slope.

34. A method as claimed in claim 33 wherein N° is approximately 10°.

* * * * *